US00PP36987P2

(12) United States Plant Patent
Green, Jr.

(10) Patent No.: US PP36,987 P2
(45) Date of Patent: Sep. 30, 2025

(54) ***CAMELLIA* PLANT NAMED 'GREEN 01-019'**

(50) Latin Name: *Camellia sasanqua*
Varietal Denomination: GREEN 01-019

(71) Applicant: Robert M Green, Jr., Fairhope, AL (US)

(72) Inventor: Robert M Green, Jr., Fairhope, AL (US)

( * ) Notice: Subject to any disclaimer, the term of this patent is extended or adjusted under 35 U.S.C. 154(b) by 0 days.

(21) Appl. No.: 19/031,512

(22) Filed: Jan. 18, 2025

(51) Int. Cl.
*A01H 6/00* (2018.01)
*A01H 5/02* (2018.01)

(52) U.S. Cl.
USPC ..... Plt./245

(58) Field of Classification Search
USPC ..... Plt./245
CPC ..... A01H 6/00; A01H 5/02
See application file for complete search history.

*Primary Examiner* — Keith O. Robinson
(74) *Attorney, Agent, or Firm* — Penny J. Aguirre

(57) ABSTRACT

A new cultivar of *Camellia sasanqua* plant named 'GREEN 01-019', that is characterized by its dense, bushy, oval-shaped and upright plant habit, its glossy, very dark green foliage, its flowers that are consistantly red in color and large in size, and its case of propagation and production.

2 Drawing Sheets

Botanical classification: *Camellia sasanqua.*
Variety denomination: 'GREEN 01-019'.

BACKGROUND OF THE INVENTION

The present invention relates to a new and distinct cultivar of *Camellia* plant, botanically known as *Camellia sasanqua*, 'GREEN 01-019'. The new cultivar will be referred to hereafter by its cultivar name, 'GREEN 01-019'. 'GREEN 01-019' is a new evergreen shrub grown for container and landscape use.

'GREEN 01-019' was derived from an ongoing breeding program conducted by the Inventor in Fairhope, Alabama. The goal of the breeding program are to develop new cultivars of *Camellia sasanqua* with true red flowers and bushier plant habits that are easy to propagate and produce. 'GREEN 01-019' originated as a seedling that arose from seed planted from open pollination of *Camellia sasanqua* cultivar 'Yuletide' (not patented) as the female parent in 1997 in Fairhope, Alabama. The male parent is therefore unknown. The new *Camellia* was selected as a single unique plant in 2001.

Asexual propagation of the new cultivar was first accomplished by stem cuttings by the Inventor in 2002 in Fairhope, Alabama. Asexual propagation by stem cuttings has determined that the characteristics of this cultivar are stable and are reproduced true to type in successive generations.

SUMMARY OF THE INVENTION

The following traits have been repeatedly observed and represent the characteristics of the new *Camellia*. These attributes in combination distinguish 'GREEN 01-019' as a new and distinct cultivar of *Camellia.*

1. 'GREEN 01-019' exhibits a dense, bushy, oval-shaped and upright plant habit.
2. 'GREEN 01-019' exhibits glossy, very dark green foliage.

3. 'GREEN 01-019' exhibits flowers that are consistantly red in color and large in size.
4. 'GREEN 01-019' exhibits ease of propagation and production.

The female parent of 'GREEN 01-019' differs from 'GREEN 01-019' in having foliage that is less glossy and lighter green in color, flowers that are smaller in size and less true red in color, and a less vigorous growth habit. 'GREEN 01-019' can also be compared to the *Camellia sasanqua* cultivars 'Kanjiro' (not patented) and 'TDN 1116' (U.S. Plant Pat. No. 14,213). Both 'Kanjiro' and 'TDN 1116' are similar to 'GREEN 01-019' in having reddish colored flowers, vigorous growth habits, and ease of propagation. 'Kanjiro' differs from 'GREEN 01-019' in having rosy red flowers, a vase-shaped and less dense growth habit, and larger sized flowers. 'TDN 11116' differs from 'GREEN 01-019' in having a much less dense plant habit and flowers that are more pink in color.

BRIEF DESCRIPTION OF THE DRAWINGS

The accompanying colored photographs illustrate the overall appearance and distinct characteristics of the new *Camellia*. The photographs were taken of a 7-year-old plant of 'GREEN 01-019' as grown outdoors in a trial garden in Mobile, Alabama.

The photograph in FIG. 1 provides a side view of 'GREEN 01-019' in bloom.

Figure 1:
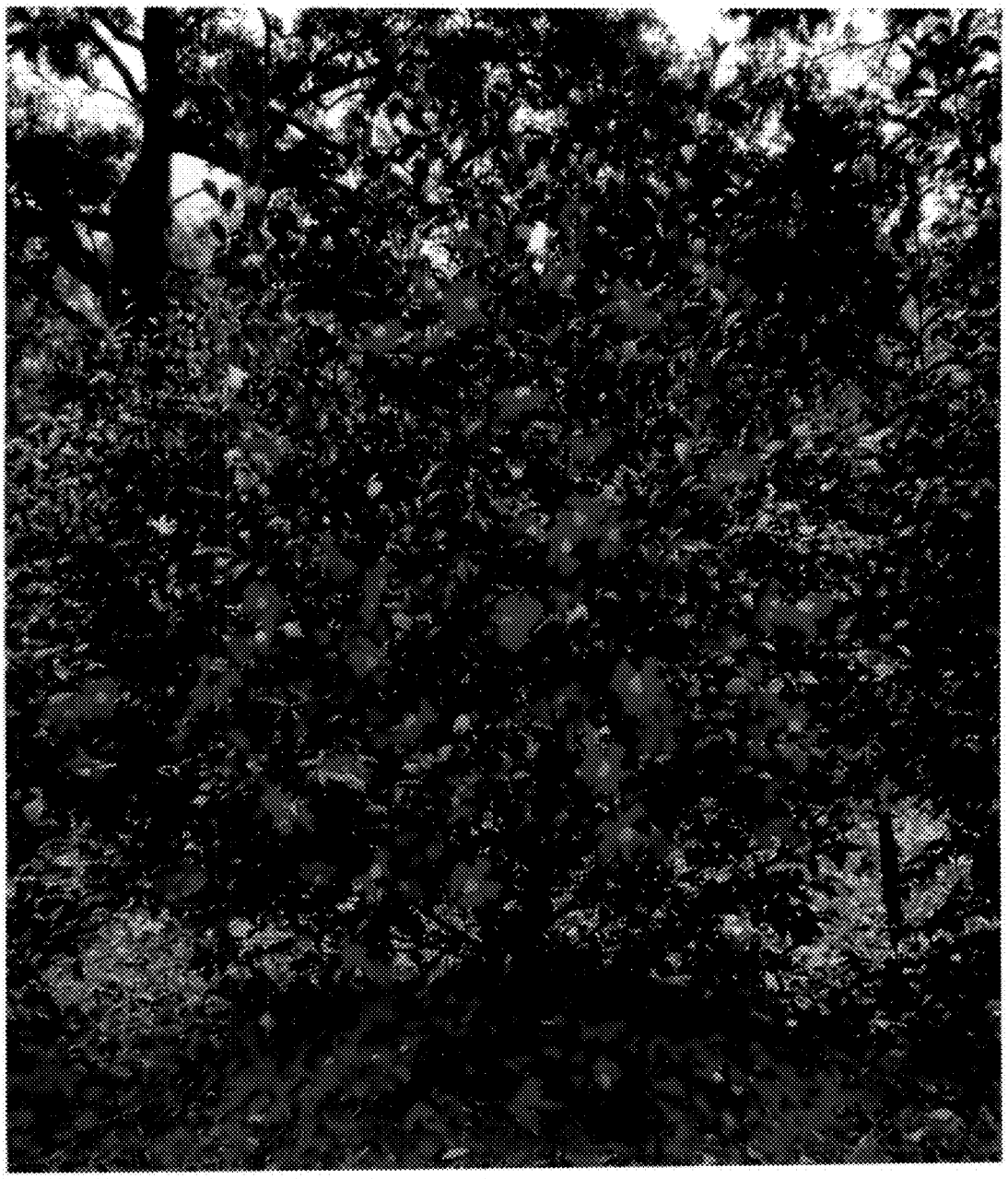
Figure 2:
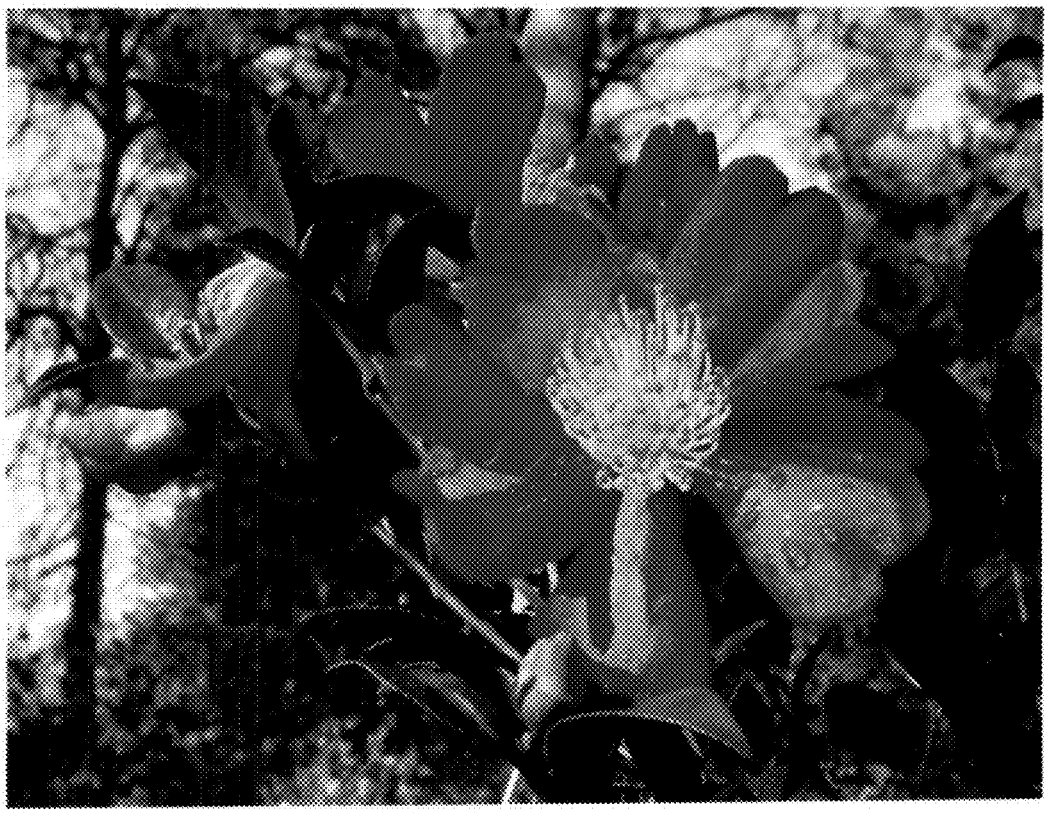

The photograph in FIG. 2 provides a close-up view of a flower of 'GREEN 01-019' in bloom.

The colors in the photographs are as close as possible with digital photography techniques available, the color values cited in the detailed botanical description accurately describe the colors of the new *Camellia.*

DETAILED BOTANICAL DESCRIPTION

The following is a detailed description of 4-year-old plants of the new cultivar as grown outdoors in 7-gallon containers in El Camp, Texas. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming habit.*—6 weeks in fall in Fairhope, Alabama.

*Plant type.*—Evergreen shrub.

*Plant habit.*—Dense, bushy, oval-shaped, upright.

*Height and spread.*—An average of 98 cm in height and 70 cm in width as a 4-year-old plant grown in a container, reaches an average of 2.3 m in height and 1.8 m in width as grown in the landscape.

*Hardiness.*—At least hardy in U.S.D.A. Zones 7b to 9.

*Diseases and pests.*—Has shown to be highly resistant to anthracnose (caused by *Glomerella cingulate*) and exhibits few production related fungus issues.

*Propagation.*—Stem cuttings.

*Time required for root initiation.*—An average of 6 to 8 weeks.

*Time required to produce a young plant from a rooted cutting.*—An average of 6 to 9 months to produce a liner.

*Growth rate and vigor.*—Vigorous.

Branch description:

*Branch shape.*—Round.

*Branch strength.*—Strong.

*Branch color.*—Young; 143A, mature; 199A.

*Branch size.*—Average of 85 cm in length, 5 mm in diameter.

*Branch surface.*—Young; glossy luster, covered with smooth bark, top is covered with soft, dense pubescence that becomes moderately pubescent as it matures, mature; covered with smooth bark, slightly rugose, and moderately glossy.

*Branching.*—Densely branched with an average of 22 main lateral branches and 6 to 12 secondary laterals per main branch.

Foliage description:

*Leaf shape.*—Elliptic.

*Leaf division.*—Simple.

*Leaf base.* Cuneate.

*Leaf apex.*—Acuminate to acute.

*Leaf fragrance.*—None.

*Leaf margins.*—Serrate.

*Leaf arrangement.*—Alternate.

*Leaf attachment.*—Petiolate.

*Leaf substance.*—Moderately thick, slightly rubbery.

*Leaf surface.*—Both surfaces are highly glossy and smooth, upper surface is very slightly rugose.

*Leaf size.*—An average of 5 cm in length and 3 cm in width.

*Leaf aspect.*—Held slightly outward from the branch, folded at the center and slightly recurved.

*Leaf quantity.*—An average of 28 per lateral branch.

*Leaf density.*—Dense.

*Leaf venation.*—Pinnate, mid rib color; upper surface 145A, lower surface; 145B.

*Leaf variegation.*—None present.

*Leaf color.*—Emerging and young upper and lower surface; a blend of 185A and 141B, after expanded; upper surface a blend of 147A and 146A, lower surface 146C, mature upper surface; 139A and 147A, mature lower surface 146B.

*Petioles.*—Flattened and curved upwards around stipule, strong, an average of 4 mm in width and 2 mm in length, a blend of 153A and 143A in color, both surfaces are glossy and densely covered with soft, pubescent hairs.

*Leaf buds.*—Lanceolate in shape, an average of 4 on terminal, an average of 1 cm in length and 4 mm in width, a blend of 162A and 184A on color, densely covered with soft, pubescent hairs.

*Stipules.*—At the base of each leaf is 1 stipule, 5 mm in length, 3 mm in width, flattened in shape, acute apex, flattened base, glabrous and glossy appearance, 184A in color.

Inflorescence description:

*Inflorescence type.*—Solitary.

*Flower number.*—4 to 5 per lateral stem.

*Flower fragrance.*—Slight honey-like fragrance.

*Flower longevity.*—About one week, self cleaning.

*Flower type.*—Semi-double.

*Flower aspect.*—Outward to slightly upright.

*Flower size.*—An average of 5 cm in diameter and 3 cm in depth.

*Peduncles.*—None, flowers are sessile to stem.

*Flower buds.*—Ovate in shape, arranged on terminal and upper axillary nodes, surface is glabrous, 2 cm in length, 1 cm in width, color; a blend of NN137A and 71B in color.

*Sepals.*—An average of 4, ovate in shape and strongly cupped inward, imbricate, an average of 1 cm in length and 1.2 cm in width, broadly acute apex, truncate base, entire margins, both surfaces are glabrous, slightly glossy and sheen, color of both surfaces; NN137A.

*Petals.*—An average of 12, obcordate in shape, an average of 3 cm in length and 2.5 cm width, apex cordate, base cuneate, margins slightly undulated, both surfaces are velvety and glabrous, color of upper and lower surface when opening and fully open; a blend of 60A and 71B.

*Petaloids.*—Not present.

*Receptacle.*—Disk-shaped, 3 mm in diameter and depth.

Reproductive organs:

*Pistil.*—1, style; is an average of 1 cm in length, 1 mm in width, 18A in color, stigmas; are four-parted with each appendage <0.5 mm in diameter and 2 mm in length, club-shaped, 1A in color, positioned slightly below stamens, and glandular in appearance, ovary; is oblong-oval in shape with pubescent surface with long silky hairs and 145C in color.

*Stamens.*—An average of 70, sasangua arrangement, filaments; an average of 1.8 cm in length, 15A in color, anthers; an average of 2 mm in width, 1 mm in depth, and 13A in color, pollen; moderate in quantity and 15A in color.

*Fruit and seed.*—None observed to date.

It is claimed:

1. A new and distinct cultivar of *Camellia* plant named 'GREEN 01-019' as herein illustrated and described.

* * * * *